United States Patent
Guerry et al.

(12) 
(10) Patent No.: US 10,806,820 B2
(45) Date of Patent: Oct. 20, 2020

(54) INJECTABLE HOMOGENEOUS AQUEOUS SOLUTION OF CHITOSAN HAVING A PH CLOSE TO THE PHYSIOLOGICAL PH

(71) Applicant: Bioxis Pharmaceuticals, Lyons (FR)

(72) Inventors: Alexandre Guerry, Les Abrets (FR); Frédéric Bertaina, Poulx (FR)

(73) Assignee: Bioxis Pharmaceuticals, Nimes (FR)

(*) Notice: Subject to any disclaimer, the term of this patent is extended or adjusted under 35 U.S.C. 154(b) by 128 days.

(21) Appl. No.: 15/568,681

(22) PCT Filed: Apr. 22, 2016

(86) PCT No.: PCT/FR2016/050953
§ 371 (c)(1),
(2) Date: Oct. 23, 2017

(87) PCT Pub. No.: WO2016/170284
PCT Pub. Date: Oct. 27, 2016

(65) Prior Publication Data
US 2018/0147320 A1    May 31, 2018

(30) Foreign Application Priority Data
Apr. 23, 2015 (FR) ..................... 15 53644

(51) Int. Cl.
| | | |
|---|---|---|
| *A61K 31/722* | (2006.01) | |
| *A61L 27/20* | (2006.01) | |
| *A61K 9/00* | (2006.01) | |
| *A61K 47/26* | (2006.01) | |
| *A61K 8/02* | (2006.01) | |
| *A61K 8/20* | (2006.01) | |
| *A61K 8/24* | (2006.01) | |
| *A61K 8/36* | (2006.01) | |
| *A61K 8/73* | (2006.01) | |
| *A61K 9/08* | (2006.01) | |
| *A61K 47/02* | (2006.01) | |
| *A61K 47/12* | (2006.01) | |
| *A61K 47/36* | (2006.01) | |

(Continued)

(52) U.S. Cl.
CPC ............ *A61L 27/20* (2013.01); *A61K 8/0204* (2013.01); *A61K 8/20* (2013.01); *A61K 8/24* (2013.01); *A61K 8/36* (2013.01); *A61K 8/736* (2013.01); *A61K 9/006* (2013.01); *A61K 9/0019* (2013.01); *A61K 9/0051* (2013.01); *A61K 9/0053* (2013.01); *A61K 9/08* (2013.01); *A61K 31/722* (2013.01); *A61K 47/02* (2013.01); *A61K 47/12* (2013.01); *A61K 47/26* (2013.01); *A61K 47/36* (2013.01); *A61L 27/047* (2013.01); *A61L 27/12* (2013.01); *A61L 27/58* (2013.01); *A61Q 19/08* (2013.01); *B01D 61/243* (2013.01); *B01D 71/10* (2013.01); *A61K 2800/52* (2013.01); *A61K 2800/91* (2013.01); *A61L 2300/232* (2013.01); *A61L 2300/236* (2013.01); *A61L 2300/252* (2013.01); *A61L 2300/256* (2013.01); *A61L 2300/402* (2013.01); *A61L 2300/414* (2013.01); *A61L 2300/416* (2013.01); *A61L 2300/43* (2013.01); *A61L 2300/604* (2013.01); *A61L 2300/802* (2013.01); *A61L 2400/06* (2013.01); *A61L 2430/02* (2013.01); *A61L 2430/06* (2013.01); *A61L 2430/24* (2013.01); *A61L 2430/34* (2013.01)

(58) Field of Classification Search
None
See application file for complete search history.

(56) References Cited

U.S. PATENT DOCUMENTS

2015/0065454 A1* 3/2015 Dupasquier ............ A61L 27/20
514/55

FOREIGN PATENT DOCUMENTS

| JP | H0269502 A | 3/1990 |
|---|---|---|
| WO | 97/09879 A1 | 3/1997 |

(Continued)

OTHER PUBLICATIONS

Montembault, A. et al., A material decoy of biological media based on chitosan physical hydrogels: application to cartilage tissue engineering, Biochimie, 2006, vol. 88, pp. 551-564.

(Continued)

*Primary Examiner* — Craig D Ricci
(74) *Attorney, Agent, or Firm* — Banner & Witcoff, Ltd.

(57) ABSTRACT

The present invention relates to an injectable homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH greater than or equal to 6.2, and advantageously between 6.2 and 7.2, said solution not containing any chitosan having a degree of acetylation greater than 20%, said solution being liquid and homogeneous at ambient temperature. The invention also relates to an aqueous solution such as previously described, characterised in that it can be prepared by a method comprising at least the following steps:—
dissolving the chitosan in water by adding acid, such as a weak acid, said weak acid being advantageously chosen from the group consisting of acetic acid, glycolic acid, lactic acid, glutamic acid, and the mixtures of same, and
readjusting the pH by dialysis, preferably at ambient temperature, in order to obtain an aqueous solution having a pH greater than or equal to 6.2, advantageously between 6.2 and 7.2, and preferably between 6.25 and 7.1.

12 Claims, 1 Drawing Sheet

(51) Int. Cl.
*A61L 27/04* (2006.01)
*A61L 27/12* (2006.01)
*A61L 27/58* (2006.01)
*A61Q 19/08* (2006.01)
*B01D 61/24* (2006.01)
*B01D 71/10* (2006.01)

(56) References Cited

FOREIGN PATENT DOCUMENTS

| WO | | 03/042250 | A1 | 5/2003 | |
|----|----|----|----|----|----|
| WO | WO 2003/042250 | | * | 5/2003 | ............ C08B 37/08 |
| WO | | 2009/150651 | A1 | 12/2009 | |
| WO | | 2013/079646 | A1 | 6/2013 | |
| WO | WO 2013/079646 | | * | 6/2013 | |

OTHER PUBLICATIONS

Montembault, A. et al., Physico-chemical studies of the gelation of chitosan in a hydroalcoholic medium, Biomaterials, 2005, vol. 26,, pp. 933-943.
Database WPI Week 199016, Thomson Scientific, London, GB; AN 1990-119697.
Fan, M. et al, Preparation and structure of chitosan soluble in wide pH range, Carbohydrate Polymers, 2009, vol. 78, No. I, pp. 66-71.
Park, J.H. et al., Synthesis and Characterization of Sugar-Bearing Chitosan Derivatives: Aqueous Solubility and Biodegradability, Biomacromolecules, 2003, vol. 4, No. 4, pp. 1087-1091.
Varum, K.M. et al., Water-solubility of partially N-acetylated chitosans as a function of pH: effect of chemical composition and depolymerisation, Carbohydrate Polymers, 1994, vol. 25, No. 2, pp. 65-70.

* cited by examiner

INJECTABLE HOMOGENEOUS AQUEOUS SOLUTION OF CHITOSAN HAVING A PH CLOSE TO THE PHYSIOLOGICAL PH

RELATED APPLICATION DATA

This application is a National Stage Application under 35 U.S.C. 371 of co-pending PCT application number PCT/FR2016/050953 designating the United States and filed Apr. 22, 2016; which claims the benefit of FR application number 15 53644 and filed Apr. 23, 2015 each of which are hereby incorporated by reference in their entireties.

The present invention relates to fillers or biological materials that can be injected into humans or animals. In particular, the present invention relates to an injectable homogeneous aqueous solution of chitosan having a pH as close as possible to the physiological pH (pH=7). The present invention also relates to compositions containing such a homogeneous aqueous solution of chitosan. The invention also relates to such compositions for use as dermatological or cosmetic compositions, or for use as a medical device, advantageously as a bioresorbable implant.

Various injectable fillers are already known, in particular for humans.

Collagen has long been the preferred filler for the face, in particular for filling wrinkles and fine lines, or for reshaping the lips. However, since being placed on the market, hyaluronic acids have become the most used products. Indeed, in addition to the biodegradability of collagen which is judged to be too rapid, there are safety problems linked to its animal origin (bovine or porcine).

The direct injection of hyaluronic acid has two advantages: an immediate mechanical filling effect and an absence of inflammatory phenomena due to its biocompatibility. However, this biocompatibility goes hand-in-hand with a rapid biodegradation that makes the product unsatisfactory, even though the product lifetime can be prolonged through the use of cross-linked hyaluronic acid.

Nevertheless, the products which are currently used most frequently in medicine and aesthetic surgery are resorbable products having a lifetime that is generally less than 12 months.

Fillers which can be termed "permanent" are also available on the market, in the sense that their bioresorption may require several years. These products contain, among other things, synthetic or biosynthetic polymers, such as acrylic derivatives, polyacrylamides, which induce a fibrous encapsulation that is important for the longevity of the filler. However, the persistence of the injected product in the tissues presents a risk of long-term complications or delayed inflammatory phenomena, for example the formation of inflammatory granulomas, cysts, etc., several months, or even several years, after injection. Today, there are other products which provide an interesting alternative: this involves PLA (polylactic acid), a polymer having a slower biodegradation than that of other natural polymers such as collagen or hyaluronic acid. It is estimated that the filler persists for up to two years after injection. These products are marketed, in particular, under the name New-Fill (or Sculptra). The main problem with this technology is that the filling effect is only visible after a period of eight weeks, which does not provide complete satisfaction for the patient.

Furthermore, the fibrosis observed during use of non-degradable products appears to be of great interest in terms of the long-term aesthetic effect, and thus so-called "semi-permanent" products have been developed which, through their uniform composition of "vector particles", have a profibrotic effect whilst remaining biodegradable. An example is the product Atlean, which provides a dispersion of TCP (tricalcium phosphate) particles in hyaluronic acid, and the product Radiesse, which provides a dispersion of calcium hydroxyapatite particles in a gel of carboxymethyl cellulose. In all cases, the vector gel ensures the immediate ascetic effect of filling, while the particles gradually generate a fibrosis which produces the long-term effect. The interest of these products, in addition to the double action mechanism (mechanical and tissue inductor), is that they are eventually completely reabsorbed.

In a particularly advantageous manner, due to its unique chemical structure, chitosan behaves with regard to the organism as a "lure" of the biological medium (A. Montembault, K. Tahiri, C. Korwin-Zmijowska, X, Chevalier, M. Corvol, A. Domard, Biochimie, 88 (2006), 551-64): it is both sufficiently "recognised" so as not to induce dangerous inflammatory reactions, as well as sufficiently "unrecognised" so was not to be degraded too rapidly. The molecule is consists of a succession of N-acetyl-D-glucosamine and D-glucosamine fragments, the first being a constituent of extracellular matrix molecules (this residue is found in hyaluronic acid, for example), and the second being completely absent from this, chitosan is therefore more difficult to degrade from a biological point of view.

The concept of using a "lure" of the biological environment is quite novel in the field of injectable substances, particularly in aesthetic medicine, and no chitosan-containing filler is currently commercially available.

Furthermore, chitosan is known in the literature to stimulate certain immunity cells, such as macrophages, which produce an increased quantity of growth factors when present. These growth factors are biological mediators which promote the production of extracellular matrix and the proliferation of fibroblasts, which are cells producing collagen fibre. Thus, chitosan promotes the synthesis of fibrous tissue, which enables long-term "biological" filling without adverse side effects, the creation or substitution of biological tissues or filling of biological tissues, for example filling of cutaneous depressions, injection in bone cartilage or in the joints).

International application WO 2013/079646, filed by the applicant, proposes in particular an injectable homogeneous aqueous solution of chitosan, containing a chitosan having a degree of acetylation less than 20%, said aqueous solution having a pH less than 6.2. These formulations exhibit very good results and good injectability properties at the values of pH less than 6.2. However, as explained in the application, it is necessary to maintain a pH less than 6.2 in order to avoid gelling of these solutions. Indeed, a chitosan having a degree of acetylation less than 20% such as that used in these injectable formulations, is sensitive to pH, and has the peculiarity of being soluble in liquid form in aqueous solution at pH values less than 6.2, but gelling above a pH of 6.2.

However, when it is desired to inject a solution of chitosan directly into tissues having a physiological pH (between 6.8 and 7.4), it would be desirable to use a solution having a pH as close as possible to the physiological pH, in order to avoid necrosis of the tissues due to the acidity of the injected formulation.

WO 2009/150651 proposes formulating chitosan-based compositions, the pH of which is close to the physiological pH, by combining, in an injectable hydrogel, a highly acetylated chitosan that is soluble at the physiological pH with a highly deacetylated chitosan which precipitates at a pH of around 6.5, in such a way as to obtain a mixture of chitosans with varying degrees of acetylation, the resulting mixture not precipitating at a pH greater than 6.5. However, due to their higher viscosity, these hydrogels with gelled texture have poor injectability properties (or syringeability, i.e. ease of injection due to a more or less satisfactory flow through the needle of a syringe) in comparison to compositions in the form of non-gelled liquids. In addition, the mixture of two chitosans with different degrees of acetylation is not simple to implement and may present homogeneity problems in the hydrogels obtained.

Application WO03/042250 proposes chemical modification by cross-linking of the chitosans in solution having a pH of order 6.8, said solutions being prepared and maintained in liquid form at very low temperatures (4° C.), in order to allow their gelling at 37° C. It is therefore both the chemical modification of the chitosan, as well as an increase in the temperature, which enables the gelling of solutions at 37° C. to be controlled. However, within the context of this application, neutral solutions of chitosan can only be obtained by holding the solutions at a very low temperature (of order 4 to 5° C.), and by using a glycerophosphate buffer that is known to increase the solubility of chitosans in water and to confer thermogelling properties on the chitosan solution. Glycerophosphate can however present unacceptable problems, particularly when it is injected into biological tissues. In addition, the neutral liquid solutions obtained according to application WO03/042250 can be neither prepared nor stored at ambient temperature, which introduces significant constraints and significant additional industrial costs.

It would therefore be desirable to possess chitosan-based formulations having a pH closer to the physiological pH, and which remain liquid at ambient temperature, in particular between 20 and 25° C., in order to be easily injectable.

The present invention therefore relates, according to a first aspect, to an injectable homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH greater than or equal to 6.2, and advantageously between 6.2 and 7.2, said solution not containing chitosan having a degree of acetylation greater than 20%, said solution being liquid and homogeneous at ambient temperature.

The invention also relates, according to a second aspect, to an aqueous solution such as previously described, characterised in that it can be prepared by a method comprising at least the following steps:

dissolving the chitosan in water by adding acid, such as a weak acid, in order to obtain a homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH less than 6.2, said weak acid being advantageously chosen from the group consisting of acetic acid, glycolic acid, lactic acid, glutamic acid, and the mixtures of same, and readjusting the pH by dialysis, preferably at ambient temperature, in order to obtain an aqueous solution having a pH greater than or equal to 6.2, advantageously between 6.2 and 7.2, and preferably between 6.25 and 7.1.

The invention therefore also relates to a method for preparing an aqueous solution as previously described, comprising at least the following steps:

dissolving the chitosan in water by adding acid, such as a weak acid, in order to obtain a homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH less than 6.2, said weak acid being advantageously chosen from the group consisting of acetic acid, glycolic acid, lactic acid, glutamic acid, and the mixtures of same, and readjusting the pH by dialysis, preferably at ambient temperature, in order to obtain an aqueous solution having a pH greater than or equal to 6.2, advantageously between 6.2 and 7.2, and preferably between 6.25 and 7.1.

The homogeneous solutions of chitosan according to the present invention are temperature-stable, particularly up to 40° C., in particular between 20 and 30° C., and are therefore not thermogelling but only gel when the pH is increased. They are therefore distinguished, by this aspect, from formulations described in patent application WO03/042250. Obtaining temperature-stable solutions is particularly advantageous for industrial implementation of solutions of the invention and the storage of same.

Chitosan

Aqueous solutions according to the invention comprise at least one chitosan.

Chitosan is an aminopolysaccharide generally obtained by N-deacetylation of chitin, a polysaccharide widely found in biomass. Chitin is present, in particular, in the cuticles of arthropods, the endoskeleton of cephalopods, and the cell walls or extracellular matrix of mushrooms, yeasts or algae.

Advantageously, according to the invention, chitosan is a natural product coming from an animal source, for example from crustaceans such as crabs, shrimp or squids, or from a plant source such as mushrooms or algae. Chitosan and chitin are respectively linear copolymers of 2-acetamido-2-deoxy-D-glucopyranose and of 2-amino-2-deoxy-D-glucopyranose. It is more common to speak of N-acetyl-D-glucosamine (GlcNAc) and D-glucosamine (GlcN)), linked by β-1,4 glycosidic linkages. Chitin and chitosan are differentiated by the molar fraction (expressed in %) of GlcNAc units present in the copolymer, also referred to as the degree of acetylation (DA).

The chemical structures of chitosan and chitin are schematically represented below as a function of the degree of acetylation (DA):

N-acétyl-D-Glucosamine (GlcNAc)

D-Glucosamine (GlcN)

Degree of acetylation (DA):

$$DA(\%) = \frac{nGlcNAc}{nGlcNAc + nGlcN} \times 100$$

where nGlcNAc=number of acetylated units, and nGlcN=number of deacetylated units.

According to the present invention, chitosan has a degree of acetylation (DA) less than 20%, preferably less than 19%, more preferably less than 17%, yet more advantageously less than or equal to 15%, for example less than 10%.

Typically, chitosan according to the invention has a degree of acetylation (DA) between 0.5 and 20%, more preferably between 1 and 19%, more preferably between 1 and 17%, yet more preferably between 2 and 15% and still more preferably between 2 and 10%.

The degree of acetylation is preferably measured according to the method described in the publication "Physicochemical studies of the gelation of chitosan in a hydroalcoholic medium" A. MONTEMBAULT, C. VITON, A. DOMARD Biomaterials, 26(8), 933-943, 2005).

Chitosan used in the solutions of the invention has a weight average molecular mass (determined before sterilisation according to the method described in "Physicochemical studies of the gelation of chitosan in a hydroalcoholic medium" A. MONTEMBAULT, C. VITON, A. DOMARD Biomaterials, 26(8), 933-943, 2005) of between 100,000 and 1,500,000 g/mol, advantageously between 200,000 and 1,000,000 g/mol, more advantageously between 250,000 and 800,000 g/mol, and yet more advantageously between 300,000 and 600,000 g/mol.

Conventionally, a chitosan with molecular mass between 100,000 and 1,000,000 g·mol$^{-1}$ can also be characterised by its viscosity (conventionally at a concentration of 1% in an aqueous solution with 1% acetic acid, at 25° C.). With this consideration, the molar mass of chitosan can also be defined by a viscosity between 5 Pa·s and 20 Pa·s.

The viscosity of the composition is measured at 25° C. using a DHR1 rheometer (TA industrie) and a flat geometry of 40 mm in a dynamic mode with applied shear rate of 0.01 to 1 s$^{-1}$.

According to a preferred embodiment, the chitosan used in these solutions according to the invention is not chemically modified and, in particular, is not grafted in order to promote the solubility thereof in aqueous solution at pH values close to neutrality (between 6.2 and 7.2). It is distinguished in this sense from chitosans used in application WO03/042250 or application JP-H02-69502, in publication "Synthesis and characterization of sugar-bearing chitosan derivatives: aqueous solubility and biodegradability", Jae Hyung Park et al., Biomacromolecules 2003, 4, 1087-1091, and in the publication "Water solubility of partially N-acetylated chitosans as a function of pH: effect of chemical composition and depolymerization" Varum K. M. et al., Carbohydrate polymers 25 (1994), 65-70.

According to a particular feature, another chitosan having lower average molecular mass, advantageously less than 20,000 g/mol, can be added to the chitosan as previously defined, provided that the homogeneity of the thus obtained solution is not altered.

In this embodiment, this other chitosan can be present in the form of cross-linked chitosan particles.

Solution

The injectable homogeneous aqueous solution of chitosan according to the invention contains, in a physiologically acceptable medium, a chitosan having a degree of acetylation less than 20% and a weight average molecular mass of between 100,000 and 1,500,000 g/mol, as described above.

For the purposes of the present application, "physiologically acceptable medium" shall mean a medium which presents no risk of intolerance or toxicity during injection of the injectable solution according to the invention into biological tissues. The physiologically acceptable medium shall therefore be inert and biocompatible with respect to biological tissues such as muscles, joints, eyeballs and more generally in the soft or hard tissues of the body, for example the organs (digestive system or urogenital system) or the adipose tissues, mucous membranes, gums, cartilage, bones, etc.

The pH of the aqueous solution according to the present invention is greater than or equal to 6.2, and is advantageously between 6.2 and 7.2, preferably between 6.25 and 7.1, and more preferably between 6.3 and 7.0.

In the context of the invention, the chitosan is advantageously soluble in an aqueous solution, such as water, in the pH range mentioned above, by protonation of the amine groups of the chitosan. Advantageously, the aqueous solution according to the invention is stable, in particular stable (conservation of the rheological properties, colour, transparency and/or limpidity at 25° C. of same) during storage at temperatures between 4 and 25° C. for at least 1 month, preferably at least 6 months, and more preferably at least 24 months. In other words, even after a prolonged storage period at temperatures between 4 and 25° C., the properties at 25° C. (rheological, colour, transparency and/or limpidity) of the aqueous solution according to the invention are preserved.

For the purposes of the present invention, an injectable "solution" shall mean a composition in the form of a liquid, as opposed to a gelled composition. Hence it is distinguished from compositions in the form of injectable solubilised chitosan-based hydrogels such as those described in patent application WO 2009/150651. Due to their higher viscosity, these hydrogels with gelled texture exhibit less favourable injectability properties (or syringeability, i.e. ease of injection due to a more or less satisfactory flow through the needle of a syringe) than the liquid solutions according to the invention.

For the purposes of the present invention, "liquid" solutions shall mean a composition which flows under its own weight, in particular after at most 24 hours, preferably at most 10 hours, in contrast to a gel, and in particular a hydrogel.

Liquid solutions according to the invention preferably exhibit a viscosity at 25° C. of less than 1000 Pa·s, preferably between 20 and 800 Pa·s, more preferably between 50 and 600 Pa·s. By way of comparison, formulations in the form of hydrogels typically have a viscosity of order 4000 to 10,000 Pa·s.

The viscosity of the composition is measured at 25° C. using a DHR1 rheometer (TA industrie) and a flat geometry of 40 mm in a dynamic mode with applied shear rate of 0.01 to 1 s$^{-1}$.

The distinction between the solutions according to the invention and formulations in the form of gels can be seen in particular by the measurement of the rheological properties of these compositions.

The gel/solution distinction is made during a rheological study in oscillation from 0.1 to 100 rad·s$^{-1}$ at a constant frequency of 1 Hz at 25° C., in order to determine the viscous moduli G" and the elastic modulus G'.

Indeed, for the purposes of the present invention, a liquid solution is characterised in particular by the fact that the viscous modulus G" is greater than the elastic modulus G'. By contrast, in the case of a gel, the elastic modulus G' is greater than the viscous modulus G". The measurements are carried out on a DHR2 rheometer (TA industries) and a flat geometry 40 mm in a dynamic mode (angular frequency: 100 to 1 rad/s, deformation 1%, 37° C.). The samples, consisting of 2.5 ml of chitosan solution to be tested, are deposited in the cups, placed at 37° C. in the culture medium for 24 hours.

For the purposes of the present invention, "homogeneous" chitosan solution shall mean that all of the chitosan polymer is dissolved, the solution comprising no solid particles in suspension in the liquid phase. The solution according to the invention is typically transparent. The homogeneity of the chitosan solution can be characterised in particular by measurement of the transmittance of light through a sample of the solution. Hence, according to a preferred embodiment, the chitosan solution according to the present invention has a light transmittance value, at a wavelength equal to 500 nm, through a sample of thickness 1 cm, greater than 60%, preferably greater than 70%, more preferably greater than 80%, and yet more preferably greater than 90%. In particular, the homogeneous aqueous solution according to the invention has a transmittance between 60 and 100%, preferably between 70 and 99%, more preferably between 80 and 98%, and yet more preferably between 90 and 97%.

The homogeneous liquid solutions of chitosan which are the subject of the present invention are preferably liquid and homogeneous at ambient temperature, in other words between 20 and 25° C., preferably at 25° C. They are distinguished in this respect from intermediate solutions described in the examples of application WO03/042250, which are liquid at low temperature (4° C.) but are gelled and become turbid when the temperature is increased.

The homogeneous liquid solutions of chitosan which are the subject of the present invention are preferably stable over time during storage at 25° C. In particular, their viscosity at 25° C. and their transmittance remains stable for at least 1 hour and for up to more than 3 years, in order to allow storage of the solutions. Hence, the solutions according to the invention preferably have storage stability at 25° C. for a period of between 1 hour and 3 years, more preferably between 10 hours and 2 years, still more preferably between 1 day and 1 year, and still more preferably between 1 month and 9 months.

According to a particular feature of the present invention, the homogeneous chitosan aqueous solution contains between 0.1 and 4.5%, advantageously between 1 and 3.5%, in particular between 2 and 3.5%, chitosan by weight, with respect to the total weight of the aqueous solution.

In a particularly advantageous manner, the aqueous solution according to the invention is formulated to be administered or is used by intradermal or subcutaneous, intramuscular, intra-articular or intraocular injection, and more generally into the soft or hard tissues of the body, for example the organs (digestive system or urogenital system) or the adipose tissues, mucous membranes, gums, cartilage, bones, etc. Due to having a pH close to the physiological pH, the solution according to the invention can be injected directly into the tissues, without the risk of causing necrosis. The solution can be packaged in a syringe such as a sterile syringe.

In a particular embodiment, the aqueous solution according to the invention is sterilised before injection, for example by autoclave.

After sterilisation, the chitosan typically has a weight average molecular mass between 50,000 and 1,200,000 g/mol, advantageously between 100,000 and 1,000,000 g/mol.

After sterilisation, the liquid solutions according to the invention preferably have a viscosity less than 800 Pa·s, preferably between 5 and 800 Pa·s. The viscosity of the solutions after sterilisation is measured according to the method described for measuring the viscosity of the solutions before sterilisation.

In a particularly advantageous manner, before injection the aqueous solution according to the present invention contains no chitosan having a degree of acetylation greater than 20%. Thus, the chitosan according to the invention is not mixed with a chitosan having a degree of acetylation between 30 and 60%, such as that described in patent applications WO 2008/072230 and WO 2009/150651.

In a particular embodiment according to the present invention, the aqueous solution contains several chitosans, but with a single degree of acetylation (DA), said degree of acetylation being less than 20%, advantageously left than 10%.

In another particular embodiment of the present invention, the aqueous solution contains a chitosan such as defined above in mixture with another chitosan, such as a chitosan oligosaccharide also called a chitooligosaccharide, having a degree of acetylation less than 20%, advantageously less than 10%, in a yet more advantageous manner having a degree of acetylation identical to the chitosan as defined above, and typically having a very low weight average molecular mass, for example less than 20,000 g/mol, advantageously less than 17,000 g/mol.

In a further particular embodiment of the present invention, the aqueous solution contains, as a polymer, a single chitosan having a degree of acetylation as defined above, advantageously having an average molecular mass as defined above, advantageously with a content between 0.1 and 4.5%, advantageously between 1 and 3.5%, in particular between 2 and 3.5%, by weight of chitosan, with respect to the total weight of the aqueous solution.

Cross-Linking Agent

In a particular embodiment, the chitosan can be partially cross-linked through ionic interactions induced, for example, by the addition of sulfate, citrate, metallic anions or even anionic molecules, in particular by the formation of polyelectrolyte complexes with polysaccharides having a carboxylic $COO^-$ group (alginates, pectin, xanthan, hyaluronic acid), with polysaccharides having a sulfate group, or with polylactic acid (PLA), or by interaction with proteins (collagen), nucleic acid (DNA, RNA, siRNA, mRNA, etc.) or oxidised polysaccharides.

In another particular embodiment, the chitosan can be partially cross-linked by means of covalent cross-linking agents (e.g. genipin), excluding agents known for their toxicity, such as agents of the epoxy group (for example 1,4-butanediol diglycidyl ether—BDDE) or bifunctional or polyfunctional esters (for example ethylenediaminetetraacetic acid—EDTA), divinyl sulfone, carbodiimides, and dialdehydes.

In a particular embodiment, the aqueous solution according to the invention comprises a combination of an aqueous solution of non-cross-linked chitosan with an aqueous solution of cross-linked chitosan.

Method for Preparing the Solution

According to a particular feature, the aqueous solution according to the invention can be prepared by the following steps
- dissolving the chitosan in water by adding acid, such as a weak acid, in order to obtain a homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH less than 6.2,
- said acid being advantageously chosen from the group consisting of acetic acid, glycolic acid, lactic acid, glutamic acid, and the mixtures of same, and
- readjusting the pH by dialysis, preferably at ambient temperature, in order to obtain an aqueous solution having a pH greater than or equal to 6.2, advantageously between 6.2 and 7.2, and preferably between 6.25 and 7.1.

Before dissolving, the chitosan is typically in the form of a powder or flakes. After dissolving, the chitosan is in protonated form. This is a cationic polyelectrolyte for which the counter-ion comes from the acid used for dissolving. For example, if acetic acid is added to the water in order to dissolve the chitosan, the chitosan is found in the form of chitosan acetate, in other words a protonated $NH_3^+$ form of amine functions in electrostatic interaction with acetate ions.

The chitosan is dissolved in the water using a strong acid or a weak acid. However, the chitosan is preferably dissolved in the water using a weak acid in order to avoid its degradation by hydrolysis in acid solution (at pH values of order 3 or less obtained during solubilisation by strong acid). Strong acids, although allowing effective solubilisation of chitosan in water, are more difficult to use and require working precisely on the stoichiometry.

The strong acid can be, for example, hydrochloric acid or phosphoric acid.

The weak acid can be chosen from acetic acid, glycolic acid, lactic acid, glutamic acid, and mixtures of same.

In a particular embodiment according to the invention, during the dissolving step, the acid is added in the strictly necessary quantity for dissolving the chitosan. It is possible to use an excess of acid for certain chitosans, for example chitosans that are difficult to solublise with the strictly necessary quantity of acid, then the chitosan is precipitated again using ammonia for example. After a series of washings intended to remove the excess ammonia and the salts, the chitosan can then be freeze-dried in order to recover the dry matter. This will then be easier to solubilise.

In another particular embodiment according to the invention, during the dissolving step, the acid is added in the strictly necessary quantity for dissolving the chitosan, such as the strictly necessary stoichiometric quantity for protonation of the $NH_2$ sites.

Typically, the number of sites to be protonated is calculated in the following manner:

$$M_{monomer} = 203 \times DA + 161 \times (1-DA)$$

$$n_{NH_2} = \frac{m \times (1-DA) \times (1-\%_{H_2O})}{M_{monomer}}$$

where m=mass of raw material introduced, $\%_{H_2O}$=water content of the raw material, DA=degree of acetylation, nNH2=the number of sites to be protonated in moles. $M_{monomer}$=average molecular mass of the residues, in g·mol$^{-1}$ Control of the pH of the solutions is very important in order to avoid acid necrosis of the tissues after injection, and also to protect the solutions from hydrolysis and degradation of the chitosan if a sterilisation is performed (for example by autoclave at 121° C. for 15 minutes).

In the context of the present invention, adjustment of the pH is carried out in a very gradual manner by dialysis.

Without wishing to be bound by any theory, it appears that by adjusting the pH in a gradual manner (in particular by dialysis), as opposed to a sudden adjustment by addition of a buffer solution, it is possible to maintain the solution in liquid non-gelled form while attaining pH values closer to the physiological pH. The methods of the prior art, in which the pH adjustment is carried out by adding a compound such as sodium bicarbonate or a PBS buffer ("Phosphate Buffer Saline"—saline solution of phosphate buffer), appears to lead to too sudden a change in pH, leading to gelling of the solution from a pH of 6.2. Against all expectations, the inventors responsible for the present application have shown that by controlling the rise in pH in order to make it continuous, and gradual, it was possible to maintain the aqueous solution of chitosan in liquid form at pH values greater than 6.2, even more advantageously approaching the physiological pH.

The pH value is advantageously controlled using a pH meter during the rise in pH in order to attain a pH greater than or equal to 6.2 and advantageously between 6.2 and 7.2, preferably between 6.25 and 7.1, most preferably between 6.3 and 7.0.

The dialysis is a membrane method for separating molecules or ions in solution Thus, in the context of the present invention, the aqueous solution of chitosan according to the invention can undergo dialysis against a buffer solution having a pH equal to the final desired pH for the chitosan solution (target pH), in other words at least greater than 6.2, advantageously between 6.2 and 7.2, preferably between 6.25 and 7.1. When the buffer solution has a pH greater than the pH for gelling of the solution (for example 7.5), the dialysis should then be monitored in order to avoid gelling of the solution.

The buffer solution can, for example, be a saline solution of phosphate buffer (PBS, TBS, PBS-lactic acid), tris(tris(hydroxymethyl)methylamine), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid)), MES (2-(N-morpholino) ethanesulfonic acid (PIPES), sodium chloride (NaCl).

According to a preferred embodiment, the buffer solution is a phosphate buffer solution PBS ("Phosphate Buffer Saline"—phosphate buffer saline solution) comprising an "acid" salt $NaH_2PO_4$, a "basic" salt $Na_2HPO_4$ and NaCl.

According to a particular embodiment, the buffer is physiologically acceptable, in other words it presents no risk of intolerance or toxicity during injection of the injectable solution according to the invention into the tissues. For this purpose, the buffer is preferably not glycerophosphate and in particular not β-glycerophosphate which, although a mild irritant to the skin, poses calcification problems when injected into the tissues.

According to a particular embodiment of the invention, dialysis can be carried out in a static manner, in a single bath, against a buffer solution such as described above.

In this embodiment, the buffer solution can have a pH greater than the desired pH for the chitosan solution, for example between 7.0 and 7.5. The dialysis must then be monitored in real-time so as not to increase the pH beyond the gelling pH. However, the use of a buffer solution having too high a pH may have the disadvantage of creating a pH gradient within the dialysis pouch containing the aqueous solution of chitosan, in particular between the periphery and the centre of the pouch, which could alter the homogeneity of the chitosan solution. Moreover, if the pH gradient causes gelling of the aqueous solution of chitosan at the periphery of the membrane, this could reduce the efficiency and quality of the dialysis by limiting exchange of protons, salt and solvent between the chitosan solution and the buffer solution.

Thus, when the dialysis is carried out in a static manner, in a single bath against a buffer solution, it is preferable that said buffer solution has a pH equal to the final desired pH for the chitosan solution (target pH), for example between 6.5 and 6.9.

According to a more preferred embodiment, the dialysis can be carried out in a static manner in a plurality of successive baths, against buffer solutions having different pH values that are increasingly close to the final desired pH for the chitosan solution (target pH). It is thus possible to raise the pH in a more gradual manner as a function of the number of buffer baths used, in order to approach as close as possible to the gelling pH of the chitosan solution, without ever reaching it. However, each change of bath is accompanied by a sudden variation in pH, although of low amplitude, which is capable of destabilizing the chitosan solution and causing it to gel at pH values of order 6.3-6.4. These pH values are certainly higher than those obtained for compositions from the prior art using the addition of a buffer directly into the aqueous solution of chitosan, but can advantageously come closer to the physiological pH in order to minimise the risk of necrosis of the tissue during injection of the aqueous solution of chitosan.

Thus, according to a particular preferred embodiment, the dialysis is carried out in a dynamic manner, in other words by continuously circulating a solution, allowing the gradual increase in pH, through one or more dialysis pouches comprising a dialysis membrane enclosing the aqueous solution of chitosan.

Figure 1:
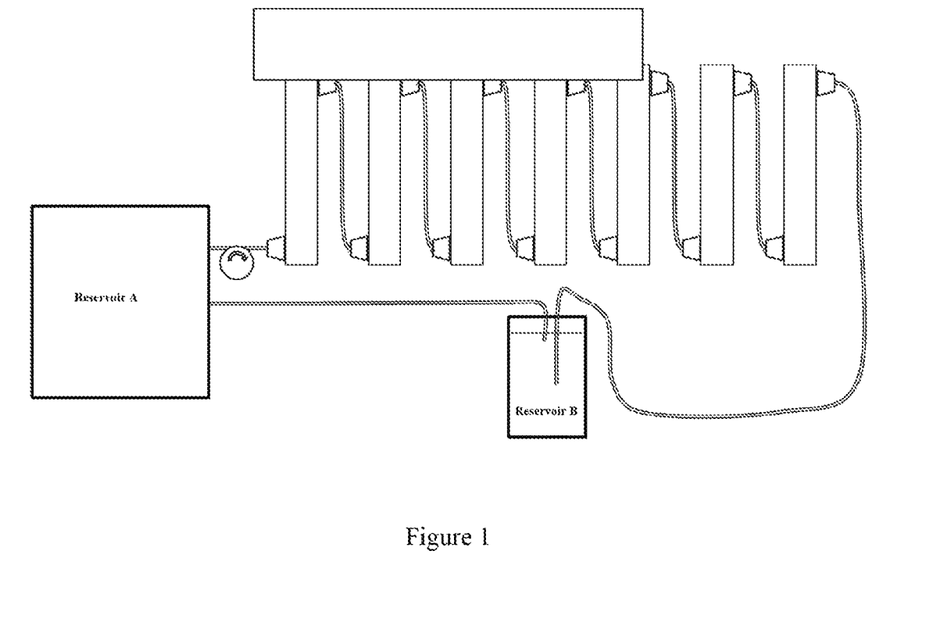
FIG. 1 is a schematic of a dialysis device containing the compositions disclosed herein and in accordance with the methods disclosed herein.

This method of dialysis utilises, in particular, a first reservoir A containing a volume $V_A$ of weak acid solution. The weak acid solution contained in reservoir A is circulated through a series of dialysis pouches connected in series or in parallel with one another. The outlet of the last pouch is connected to a second reservoir B containing a volume $V_B$ of base, which base can be the conjugate base of the weak acid used in the first reservoir A, or a stronger base. The content of the second reservoir B then flows into reservoir A, thus modifying the composition thereof. The system functions as a closed circuit, until the acid-base equilibrium is attained in reservoirs A and B, thus forming, in each reservoir, a buffer solution having determined pH. In this way, the pH of the chitosan solution contained in the dialysis pouches increases gradually until attaining that of the chosen buffer solution. Such a device is illustrated in FIG. 1.

Hence, the dynamic dialysis method according to the invention implements, in particular, the following steps:
i. preparing, in a first reservoir A, a first solution comprising a weak acid, referred to as the "weak acid solution",
ii. preparing, in a second reservoir B, a second solution comprising the conjugate base or a base stronger than the conjugate base of the weak acid used in the "weak acid solution",
iii. circulating the "weak acid solution" through one or more dialysis pockets consisting of a dialysis membrane enclosing an aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH less than 6.2,
iv. introducing said "weak acid solution" recovered at the end of the dialysis of step iii) into the second reservoir B, the composition of said second reservoir B being thus modified to a "base+ε weak acid" mixture, ε representing a very small minority quantity,
v. introducing the "base+ε weak acid" mixture of reservoir B into reservoir A, in order to obtain a "weak acid+ε base" mixture in said reservoir A,
vi. repeating steps iii, iv, and v until the acid-base equilibrium is attained in reservoirs A and B, thus forming, in each reservoir, a buffer solution having determined pH.

The weak acid solution contained in reservoir A can comprise in particular any weak acid, preferably weaker than the acid used for dissolving the chitosan.

Preferably, the weak acid used in the solution of reservoir A is chosen from dihydrogen phosphate ($H_2PO_4^-$), 4-(2-hydroxyethyl)-1-piperazine ethane sulfonic acid, 2-[[1,3-dihydroxy-2-(hydroxymethyl)propane-2-yl]amino]ethanesulfonic acid, 3-(N-morpholino)propanesulfonic acid, piperazine-N,N'-bis(2-ethanesulfonic) acid, 2-(N-morpholino)ethanesulfonic acid, the carboxylic acids such as acetic acid, and glycolic acid. More preferably, the weak acid used in reservoir A is a mixture of dihydrogen phosphate ($H_2PO_4^-$) and NaCl.

In order to simultaneously control the osmolarity of the chitosan solution, the weak acid used in the solution of reservoir A can be associated with a so-called neutral salt, in other words not interacting with the acid-base pair contained in reservoirs A and B, in particular a sodium salt (NaCl) or potassium salt (KCl).

The basic solution contained in reservoir B comprises the conjugate base or a stronger base than the conjugate base of the weak acid used in the weak acid solution utilised in the solution of reservoir A. Hence, when dihydrogen phosphate ($H_2PO_4^-$) is the weak acid used in reservoir A, hydrogen phosphate ($HPO_4^{2-}$) can be used in reservoir B. The acid-base pair is chosen in such a way that its pKa is close to the desired pH for the buffer solution (+/−1). In particular, the pKa of the acid-base pair can be advantageously between 5.3 and 8.2, preferably between 5.5 and 7.5.

The dialysis pouches comprise a dialysis membrane enclosing the aqueous solution of chitosan. The dialysis membrane can, for example, be made of a regenerated cellulose polymer (natural cellulose transformed by a series of chemical and physical operations) or a cellulose ester (for example cellulose acetate) with an exclusion threshold between 5 kDa and 30 kDa.

A system of pumps can in particular ensure the continuous circulation of the weak acid solution contained in reservoir A and the conjugate base contained in reservoir B.

An agitation system can be used in the two reservoirs A and B. In reservoir A, this enables the solution to be homogenised and to avoid variations in pH linked to the introduction of a part (ε) of the solution contained in reservoir B. In reservoir B, the agitation is particularly useful when the base used this in the form of a salt. The agitation thus allows the gradual solubilisation of the basic salt. The use of a base in the form of a salt therefore makes it possible to further slow the rise in pH and therefore to ensure a still more gradual dialysis.

At the end of the dynamic dialysis method, the acid-base equilibrium is attained in reservoirs A and B, thus forming, in each reservoir, an AB buffer solution of determined pH.

The weak acid content used in reservoir A and the conjugate base content used in reservoir B are calculated by methods known to a person skilled in the art, in order to obtain, after the acid-based equilibrium has been re-established, an AB buffer solution having the desired pH.

The total volume of the AB buffer solution ($V_{AB}=V_A+V_B$) preferably represents at least 5 times the volume of the aqueous solution of chitosan to undergo dialysis, preferably at least 10 times.

The volume $V_A$ of acid solution preferably represents 100 times the volume $V_B$ of conjugate base or of stronger base than the conjugate base of the weak acid used in the first reservoir A. Indeed, the more concentrated or strong the base used in reservoir B, the more rapid the dialysis. In order to slow the dialysis, it is preferred, in the context of the invention, to increase the volume $V_B$ of reservoir B to the constant volume Va of reservoir A.

The continuous circulation of solutions A and B, the precursors of the AB buffer solution, enables a gradual increase in pH (and osmolarity when salts are used) of the chitosan solution allowing physiological values to be approached. The kinetic adjustment of the pH can be controlled by modifying the speed of circulation of solutions A and B.

The dynamic dialysis method has at least one of the following advantages:
 avoiding the formation of a film of gelled chitosan on the dialysis membrane
 not resulting in physiochemical breakdown in the chitosan solution, which could compromise its stability
 tending more easily to the gelling pH without causing gelling; and approaching this region more closely
 increasing the reproducibility of the tests
 avoiding the need for continuous control of pH during dialysis
 increasing the homogeneity of the chitosan solution and therefore of the syringes after distribution, facilitating sterilisation (identical content in each syringe).
 limiting the handling of dialysis membranes and therefore limiting the risk of contamination
 and limiting human actions and therefore the cost of dialysis.

After injection, in particular in the tissues, the homogeneous aqueous solution according to the present invention will advantageously form a semi-crystalline system, in particular due to the change in pH linked to the influence of the buffered media of the organism.

A "semi-crystalline system" shall typically mean a system consisting of a crystalline phase and a non-crystalline (amorphous) phase.

Typically, the crystals of chitosan obtained correspond to the hydrated allomorph of chitosan.

In a particularly advantageous manner according to the invention, the aqueous solution has good biocompatibility and is bioresorbable. In particular, the product according to the invention has a sufficiently long bioresorption for a prolonged filling effect, such as a prolonged filling effect.

"Bioresorbable" or "bioresorption" shall mean a biodegradation which leads to a total or essentially total degradation of the injected product.

According to a particular feature of the present invention, the chitosan solution is fluid before injection, rapidly gels (in several minutes to several hours) in situ, and has a long resorption time once injected, typically several weeks to several months, for example of order 3 or 4 weeks to 12 to 18 months. The product or biomaterial consisting of or containing the aqueous solution according to the invention has the bacteriostatic and fungistatic nature of chitosan, well-known in the field of the agri-food industry and wound dressings. These properties facilitate the preservation of the product and contribute to limiting the risks of infection connected to injection, or delayed inflammatory phenomena for other products as those mentioned above. Of all the natural molecules currently used for filling wrinkles (collagen, hyaluronic acid), chitosan is the only one to present such properties. Furthermore, the product or biomaterial consisting of or containing the aqueous solution according to the invention ensures immediate advantageous effective biological filling: the chitosan in effect promoting the synthesis of collagen, enables filling of cutaneous faults such as wrinkles by stimulation of natural mechanisms.

The present invention also relates to an injectable homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH greater than or equal to 6.2, and advantageously between 6.2 and 7.2, said solution not containing chitosan having a degree of acetylation greater than 20%, said solution being liquid and homogeneous at ambient temperature, for use in the creation or substitution of biological tissues, for example as implants, or for filling of biological tissues, for example filling of cutaneous depressions, injection into bone cartilages or into the joints.

Advantageously, the solution and the chitosan are as defined above.

In particular, the chitosan has a weight average molecular mass between 100,000 and 1,500,000 g/mol, advantageously between 200,000 and 1,000,000 g/mol, more advantageously between 250,000 and 800,000 g/mol, and yet more advantageously between 300,000 and 600,000 g/mol.

Typically, the aqueous solution does not contain any chitosan having a degree of acetylation greater than 20%.

Advantageously, said aqueous solution is able to be prepared according to the steps of the method mentioned above.

The present invention also relates to a composition comprising an aqueous solution according to the invention, and optionally an acceptable excipient or compound.

In a particular embodiment, the aqueous solution of chitosan according to the invention advantageously comprises a salt such as sodium chloride, or any other acceptable excipient, in order to adjust the osmolarity of the composition. The addition of a salt such as sodium chloride can be useful for obtaining an isotonic solution.

According to a particular feature of the present invention, the composition can additionally comprise at least one compound having known therapeutic activity. Examples include an analgesic compound, local anaesthetic such as lidocaine, mepivacaine, bupivacaine or ropivacaine, an angiogenic compound, a vaccine, a hormone, or even an active compound such as a growth factor or bioactive oligosaccharide, for example an hyaluronic acid oligosaccharide or chitosan oligosaccharide having a degree of polymerisation less than 20, or even a nucleic acid, a protein or an anti-cancer agent.

The present invention also relates to such a compound or aqueous solution according to the invention, for use as a dermatological or cosmetic composition, or even for use as a medical device, advantageously as a bioresorbable implant.

The present invention also relates to the cosmetic use or a method of cosmetic or aesthetic treatment of the human body or face, comprising injection of a composition or aqueous solution according to the invention.

The present invention also relates to the use of such an aqueous solution as a vector for active substances, for example as a vehicle for vaccines, anti-cancer agents or hormones.

In a particular embodiment, the composition or aqueous solution according to the present invention is intended to be used in the repair or reconstruction of tissues.

In particular, the composition or aqueous solution according to the present invention can be used for the creation or substitution of biological tissues, for example as implants, or for filling of biological tissues, for example injection into bone cartilages or into the joints, or for filling cavities of the body or face, such as wrinkles and fine lines, in order to create or increase volumes of the human face or body, or even for healing the skin.

According to other particular embodiments, the composition or aqueous solution according to the present invention can be used:
- in surgery, particularly in the repair of organs, or in ascetic surgery or medicine,
- in urology, particularly for the treatment of urinary incontinence,
- in infection, particularly as a fluid vector for vaccines,
- in ophthalmology, particularly for corneal healing,
- in odontology, particularly for the installing of dental implants or bone repair,
- in orthopaedics, particularly in the periosteum for volume creation or in angiology.

The composition or aqueous solution according to the present invention can also be used in rheumatology.

Advantageously, the composition or aqueous solution according to the present invention can also be used as a vector for an active substance, in particular a therapeutic active substance such as a vaccine or a hormone such as insulin or oestrogen, and more generally for all active substances for which controlled and/or prolonged delivery or release presents an advantage.

The present invention also relates to the cosmetic use of an aqueous solution or a composition according to the invention for treating or combating ageing of the skin.

Finally, the present invention also relates to a method for increasing the solubility in water of a chitosan having a degree of acetylation less than 20% and a weight average molecular mass between 100,000 and 1,500,000 g/mol as described above, comprising at least the following steps:
- dissolving the chitosan in water by adding acid, such as a weak acid, in order to obtain a homogeneous aqueous solution of chitosan containing, in a physiologically acceptable medium, a chitosan having a degree of acetylation less than 20% and a weight average molecular mass of between 100,000 and 1,500,000 g/mol, said solution containing between 0.1 and 4.5% by weight of chitosan, said solution having a pH less than 6.2, said acid being advantageously chosen from the group consisting of acetic acid, glycolic acid, lactic acid, glutamic acid, and the mixtures of same, and
- readjusting the pH by dialysis, preferably at ambient temperature, in order to obtain an aqueous solution having a pH greater than or equal to 6.2, advantageously between 6.2 and 7.2, and preferably between 6.25 and 7.1.

The steps of the present method being described in detail above.

The following examples are intended to illustrate the invention, without in any way limiting the scope.

EXAMPLE 1: PREPARATION OF AN AQUEOUS SOLUTION OF CHITOSAN

Acid Solution of Chitosan:

An aqueous solution of chitosan was prepared by dissolving solid chitosan in water acidified by acetic acid.

The chitosan used is a chitosan having molecular mass Mw between 400,000 and 1,500,000 g·mol$^{-1}$ and degree of acetylation=5%.

The viscosity, measured at a concentration of 1% in aqueous solution, with 1% acetic acid at 25° C., is 9.578 Pa·s 1.5 g of chitosan were dissolved in 500 μL of glacial acetic acid and 49.5 mL of PBS buffer ("phosphate buffered saline" with pH=6.5) comprising NaCl, an "acid" salt $NaH_2PO_4$ and a "basic" salt $Na_2HPO_4$.

The pH of the solution was 5.45.

Dialysis Equipment:

The dialysis was carried out using SpectraPor 4 regenerated cellulose membranes with a segregation of 12-14,000 Da.

The pH values were measured using a portable FiveGo FG2 pH meter (Mettler Toledo).

A PBS phosphate buffer ("phosphate buffered saline" with pH=6.5) was used.

The dialysis was performed against 3 L of regularly renewed buffer. The dialysis was stopped at the first signs of gelling.

Figure 2:
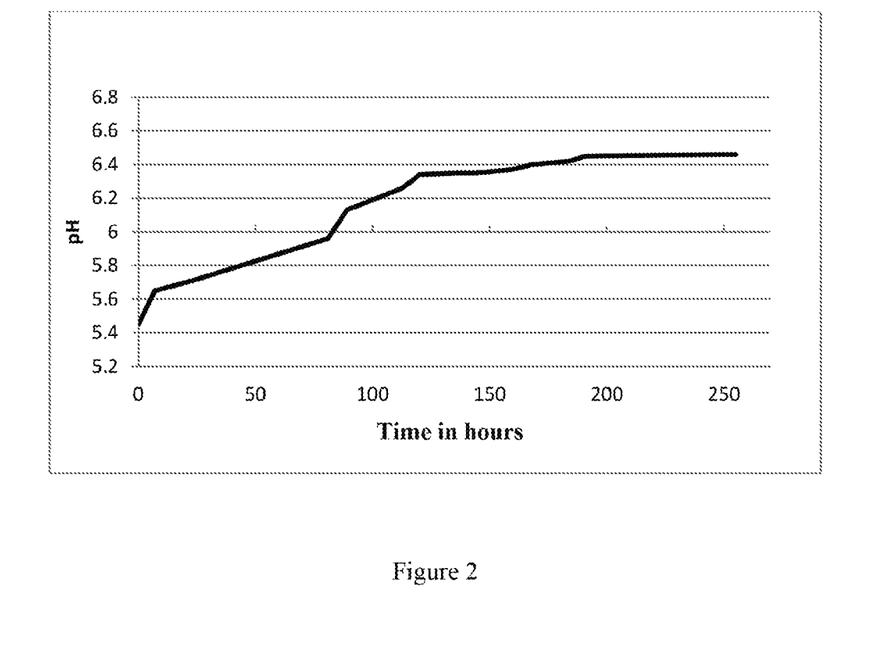
FIG. 2 graphically depicts the pH of the measured chitosan solution and the respective change over time in accordance with the composition and methods disclosed herein.

The pH of the chitosan solution was measured regularly and the change over time is illustrated in FIG. 2.

The pH of the chitosan solution was thus able to be increased up to a value of 6.46, without any sign of gelling of the solution.

EXAMPLE 2: COMPARISON

The applicant attempted to reproduce the homogeneous solution of chitosan described in example 1 of patent application WO03/042250.

In order to do this, a chitosan having a degree of deacetylation of 84% was used.

2.34 g of chitosan (deacetylated to 84%) was dissolved under agitation in 100 ml of a HCl solution (0.1 M). After 30 minutes agitation, a homogeneous solution of chitosan was obtained.

The chitosan solution was cooled in a refrigerator to 4° C. and held in an ice bath.

The pH was adjusted to 6.8 by addition, always at 4° C., of an αβ-glycerophosphate disodium salt. 1.0 g of αβ-glycerophosphate disodium salt was sufficient to attain the desired pH of 6.8.

However, the αβ-glycerophosphate salts dispersed very poorly in the chitosan solutions, despite manual and mechanical agitation. Gel inclusions appeared very rapidly around the least soluble crystals of glycerophosphate.

Hence it was not possible to obtain homogeneous aqueous solutions of chitosan having a pH of 6.8 by reproducing example 1 of document WO03/042250.

In order to resolve this problem, the applicant reproduced this test by replacing the αβ-glycerophosphate disodium salt with a β-glycerophosphate disodium salt, for which the improved chitosan solubility properties are well-known.

For this new test, the same chitosan having a degree of deacetylation of 84% was used.

2.34 g of chitosan (deacetylated to 84%) was dissolved under agitation in 100 ml of a HCl solution (0.1 M).

The chitosan solution was cooled in a refrigerator to 4° C. and held in an ice bath.

The pH was adjusted to 6.8 by gradual addition, always at 4° C., of 2.84 g of a β-glycerophosphate disodium salt dispersed by manual agitation.

A homogeneous solution of chitosan at 3.4° C., having a pH of 6.8, was thus obtained. The transmittance of the solution before and after addition of β-glycerophosphate was also measured by light diffusion, at a wavelength equal to 500 nm, through a sample of thickness 1 cm.

The solution was then heated in a bain marie until a temperature of 25° C. (ambient temperature) was attained, and was held at this temperature for 17 hours. The composition obtained was gelled and had a pronounced whitish appearance. The transmittance could no longer be measured due to the compact nature of the gel obtained.

The results are presented in the table below:

|  | Without addition of β-GP | With addition of β-GP |
| --- | --- | --- |
| 4° C. (T = 0) | T° = 3.4° C. pH = 6.02 T % = 100% Liquid | T° = 3.1° C. pH = 6.81 T % = 77% Liquid |
| 25° C. (17 hours) | T° = 24.5° C. pH = 5.60 T % = 100% Liquid | T° = 24.2 pH = 6.81 T % = impossible, gel too compact. Compact gel |

Hence, the solution obtained using example 1 of document WO03/042250, modified by the use of a β-glycerophosphate disodium salt in place of an αβ-glycerophosphate disodium salt, is indeed liquid and rather homogeneous (transmittance 77%) at low temperature (4° C.).

However, increasing the temperature to attain 25° C. (ambient temperature) leads to a gelling of the composition. In WO03/042250, chemical grafting of the chitosan makes it possible to obtain an injectable solution at 25° C. Without this grafting, the compositions described in WO03/042250 are in the form of a gel at 25° C. and can only be injectable at 4° C.

Conversely, the homogeneous aqueous solutions according to the present invention are in the form of an injectable liquid solution even at ambient temperature (20-25° C.), and only gel when the pH increases in situ.

The invention claimed is:

1. An injectable homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH greater than 6.3, said solution not containing any chitosan having a degree of acetylation greater than 20%, said solution being liquid and homogeneous at ambient temperature, wherein the solution is prepared by a method comprising the following steps:
    (1) dissolving the chitosan in water by adding acid in order to obtain a homogeneous aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH less than 6.3, wherein said acid is selected from the group consisting of acetic acid, glycolic acid, lactic acid, and glutamic acid, and the mixtures of same; and
    (2) readjusting the pH by dialysis in order to obtain an aqueous solution having a pH greater than or equal to 6.3, wherein said step is performed at a continuous and gradual rate to maintain the aqueous solution of chitosan in liquid form at pH values greater than 6.3.

2. The aqueous solution according to claim 1, characterized in that the chitosan has a degree of acetylation less than 19%.

3. The aqueous solution according to claim 1, characterized in that it contains between 1 and 3.5% by weight of chitosan, with respect to the total weight of the aqueous solution.

4. The aqueous solution according to claim 1, characterized in that the chitosan has a weight average molecular mass between 200,000 and 1,000,000 g/mol.

5. The aqueous solution according to claim 1, characterized in that it has a pH between 6.3 and 7.1.

6. The aqueous solution according to claim 1, characterized in that during the dissolving step, the acid is added in a strictly necessary quantity for dissolving the chitosan.

7. The aqueous solution according to claim 1, characterized in that it is dialyzed against a buffer solution having a pH greater than 6.3.

8. The aqueous solution according to claim 7, characterized in that the buffer solution is a phosphate-buffered saline solution comprising $NaH_2PO_4$, $Na_2HPO_4$ and NaCl.

9. The aqueous solution according to claim 7, characterized in that the dialysis is dynamic, implementing in particular the following steps:

i. preparing, in a first reservoir A, a first solution comprising a weak acid, referred to as the "weak acid solution", ii. preparing, in a second reservoir B, a second solution comprising the conjugate base or a base stronger than the conjugate base of the weak acid used in the "weak acid solution", iii. circulating the "weak acid solution" through one or more dialysis pockets consisting of a dialysis membrane enclosing an aqueous solution of chitosan containing, in a physiologically acceptable medium, between 0.1 and 4.5% by weight of a chitosan having a degree of acetylation less than 20% and a weight average molecular mass of between 100,000 and 1,500,000 g/mol, said solution having a pH less than 6.3, iv. introducing said "weak acid solution" recovered at the end of the dialysis of step iii) into the second reservoir B, the composition of said second reservoir B being thus modified to a "base+ε weak acid" mixture, ε representing a very small minority quantity, v. introducing the "base+ε weak acid" mixture of reservoir B into reservoir A in order to obtain a "weak acid+ε base" mixture in said reservoir A, vi. repeating steps iii, iv, and v until the acid-base equilibrium is attained in reservoirs A and B, thus forming, in each reservoir, a buffer solution having determined pH.

10. The aqueous solution according to claim 6, characterized in that the weak acid used in reservoir A is a mixture of dihydrogen phosphate ($H_2PO_4^-$) and NaCl and the base used in reservoir B is hydrogen phosphate ($HPO_4^{2-}$).

11. The aqueous solution according to claim 9, wherein the dialysis membrane comprises regenerated cellulose polymer or a cellulose ester with an exclusion threshold between 5 kDa and 30 kDa.

12. A composition comprising an aqueous solution according to claim 1, and optionally a compound or an acceptable excipient.

* * * * *